(12) United States Patent
Jeong et al.

(10) Patent No.: US 7,109,233 B2
(45) Date of Patent: Sep. 19, 2006

(54) PROTEASE INHIBITORS

(75) Inventors: Jae U. Jeong, Collegeville, PA (US); Dennis S. Yamashita, Collegeville, PA (US)

(73) Assignee: SMithKline Beecham Corporation, Philadelphia, PA (US)

( * ) Notice: Subject to any disclaimer, the term of this patent is extended or adjusted under 35 U.S.C. 154(b) by 0 days.

(21) Appl. No.: 10/515,118

(22) PCT Filed: May 21, 2003

(86) PCT No.: PCT/US03/16127

§ 371 (c)(1),
(2), (4) Date: Nov. 18, 2004

(87) PCT Pub. No.: WO03/104257

PCT Pub. Date: Dec. 18, 2003

(65) Prior Publication Data

US 2005/0234038 A1 Oct. 20, 2005

Related U.S. Application Data

(60) Provisional application No. 60/382,479, filed on May 22, 2002.

(51) Int. Cl.
C07D 267/02 (2006.01)
C07D 513/00 (2006.01)
C07D 515/00 (2006.01)
A61K 31/38 (2006.01)

(52) U.S. Cl. ..................... 514/430; 540/488; 540/492; 540/484; 540/485; 540/490; 514/431

(58) Field of Classification Search ................ 540/484, 540/485, 488, 490; 514/430, 431
See application file for complete search history.

(56) References Cited

U.S. PATENT DOCUMENTS

| | | | | |
|---|---|---|---|---|
| 5,002,773 A | * | 3/1991 | Keshary et al. | 424/448 |
| 5,200,773 A | * | 4/1993 | Volk | 351/219 |
| 6,306,891 B1 | * | 10/2001 | Selnick et al. | 514/423 |
| 6,380,249 B1 | * | 4/2002 | Young et al. | 514/530 |
| 6,525,042 B1 | * | 2/2003 | Kobayashi et al. | 514/212.03 |
| 6,921,759 B1 | * | 7/2005 | Anthony et al. | 514/211.03 |

* cited by examiner

*Primary Examiner*—Sabiha N. Qazi
(74) *Attorney, Agent, or Firm*—Andrea V. Lockenour; Edward R. Gimni; Charles M. Kinzig

(57) ABSTRACT

This invention relates in general to certain substituted substituted 1,1,4-11$^6$-trioxo[1,2]thiazepan-4-ylamides of formula I

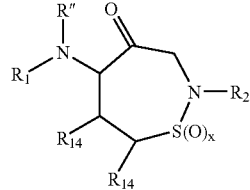

as defined herein which are protease inhibitors.

14 Claims, No Drawings

PROTEASE INHIBITORS

This application is a 371 National Phase entry of PCT/US03/16127 filed May 21, 2003 which claims priority to U.S. Provisional Application Ser. No. 60/382,479 filed May 22, 2002.

BACKGROUND OF INVENTION

This invention relates in general to certain substituted 1,1,4-11$^6$-trioxo[1,2]thiazepan-4-ylamides which are protease inhibitors. More particularly they are inhibitors of cysteine and serine proteases, particularly compounds which inhibit cysteine proteases. More specifically these compounds inhibit cysteine proteases of the papain superfamily, including, in particular those of the cathepsin family, most particularly cathepsin K. Such compounds are useful for treating diseases in which cysteine proteases are implicated, especially diseases of excessive bone or cartilage loss, e.g., osteoporosis, periodontitis, and arthritis; and certain parasitic diseases, e.g., malaria.

Cathepsins are a family of enzymes which are part of the papain superfamily of cysteine proteases. Cathepsins B, H, L, N and S have been described in the literature. Recently, cathepsin K polypeptide and the cDNA encoding such polypeptide were disclosed in U.S. Pat. No. 5,501,969 (called cathepsin O therein). Cathepsin K has been recently expressed, purified, and characterized. Bossard, M. J., et al., (1996) J. Biol. Chem. 271, 12517–12524; Drake, F. H., et al., (1996) J. Biol. Chem. 271, 12511–12516; Bromme, D., et al., (1996) J. Biol. Chem. 271, 2126–2132.

Cathepsin K has also been variously denoted as cathepsin O or cathepsin O2 in the literature. The designation cathepsin K is considered to be the most appropriate one.

Cathepsins function in the normal physiological process of protein degradation in animals, including humans, e.g., in the degradation of connective tissue. However, elevated levels of these enzymes in the body can result in pathological conditions leading to disease. Thus, cathepsins have been implicated as causative agents in various disease states, including but not limited to, infections by *pneumocystis carinii, trypsanoma cruzi, trypsanoma brucei* and *Crithidia fusiculata*; as well as in schistosomiasis, malaria, tumor metastasis, metachromatic leukodystrophy, muscular dystrophy, amytrophy, and the like.—See International Publication Number WO 94/04172, published on Mar. 3, 1994, and references cited therein. See also European Patent Application EP 0 603 873 A1, and references cited therein. Two bacterial cysteine proteases from *P. gingivallis*, called gingipains, have been implicated in the pathogenesis of gingivitis. Potempa, J., et al. (1994) Perspectives in Drug Discovery and Design, 2, 445–458.

Cathepsin K is believed to play a causative role in diseases of excessive bone or cartilage loss. Bone is composed of a protein matrix in which spindle- or plate-shaped crystals of hydroxyapatite are incorporated. Type I collagen represents the major structural protein of bone comprising approximately 90% of the protein matrix. The remaining 10% of matrix is composed of a number of non-collagenous proteins, including osteocalcin, proteoglycans, osteopontin, osteonectin, thrombospondin, fibronectin, and bone sialoprotein. Skeletal bone undergoes remodelling at discrete foci throughout life. These foci, or remodelling units, undergo a cycle consisting of a bone resorption phase followed by a phase of bone replacement.

Bone resorption is carried out by osteoclasts, which are multinuclear cells of hematopoietic lineage. The osteoclasts adhere to the bone surface and form a tight sealing zone, followed by extensive membrane ruffling on their apical (i.e., resorbing) surface. This creates an enclosed extracellular compartment on the bone surface that is acidified by proton pumps in the ruffled membrane, and into which the osteoclast secretes proteolytic enzymes. The low pH of the compartment dissolves hydroxyapatite crystals at the bone surface, while the proteolytic enzymes digest the protein matrix. In this way, a resorption lacuna, or pit, is formed. At the end of this phase of the cycle, osteoblasts lay down a new protein matrix that is subsequently mineralized. In several disease states, such as osteoporosis and Paget's disease, the normal balance between bone resorption and formation is disrupted, and there is a net loss of bone at each cycle. Ultimately, this leads to weakening of the bone and may result in increased fracture risk with minimal trauma.

Several published studies have demonstrated that inhibitors of cysteine proteases are effective at inhibiting osteoclast-mediated bone resorption, and indicate an essential role for cysteine proteases in bone resorption. For example, Delaisse, et al., Biochem. J., 1980, —192, 365, disclose a series of protease inhibitors in a mouse bone organ culture system and suggest that inhibitors of cysteine proteases (e.g., leupeptin, Z-Phe-Ala-CHN2) prevent bone resorption, while serine protease inhibitors were ineffective. Delaisse, et al., Biochem. Biophys. Res. Commun., 1984, 125, 441, disclose that E-64 and leupeptin are also effective at preventing bone resorption in vivo, as measured by acute changes in serum calcium in rats on calcium deficient diets. Lerner, et al., J. Bone Min. Rest, 1992, 7, 433, disclose that cystatin, an endogenous cysteine protease inhibitor, inhibits PM stimulated bone resorption in mouse calvariae. Other studies, such as by Delaisse, et al., Bone, 1987, —8, 305, Hill, et al., J. Cell. Biochem., 1994, 56, 118, and Everts, et al., J. Cell. Physiol., —1992, 150, 221, also report a correlation between inhibition of cysteine protease activity and bone resorption. Tezuka, et al, J. Biol. Chem., 1994, 269, 1106, Inaoka, et al., Biochem. Biophys. Res. Commun., 1995, 206, 89 and Shi, et al., FEBS Lett., 1995, 357, 129 disclose that under normal conditions cathepsin K, a cysteine protease, is abundantly expressed in osteoclasts and may be the major cysteine protease present in these cells.

The abundant selective expression of cathepsin K in osteoclasts strongly suggests that this enzyme is essential for bone resorption. Thus, selective inhibition of cathepsin K may provide an effective treatment for diseases of excessive bone loss, including, but not limited to, osteoporosis, gingival diseases such as gingivitis and periodontitis, Paget's disease, hypercalcemia of malignancy, and metabolic bone disease. Cathepsin K levels have also been demonstrated to be elevated in chondroclasts of osteoarthritic synovium. Thus, selective inhibition of cathepsin K may also be useful for treating diseases of excessive cartilage or matrix degradation, including, but not limited to, osteoarthritis and rheumatoid arthritis. Metastatic neoplastic cells also typically express high levels of proteolytic enzymes that degrade the surrounding matrix. Thus, selective inhibition of cathepsin K may also be useful for treating certain neoplastic diseases.

We have now discovered a novel class of substituted 1,1,4-11$^6$-trioxo[1,2]thiazepan-4-ylamides which are protease inhibitors, most particularly of cathepsin K.

SUMMARY OF INVENTION

The present invention provides substituted 1,1,4-11$^6$-trioxo[1,2]thiazepan-4-ylamide-derived protease inhibitors which inhibit the likes of cathepsin K, and which are useful for treating diseases which may be therapeutically modified by altering the activity of such proteases.

Accordingly, in the first aspect, this invention provides a compound according to Formula I.

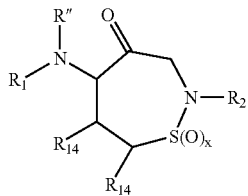

I wherein:

"X" in the group S(O), is 0, 1 or 2;

$R_1$ is either formula A or B

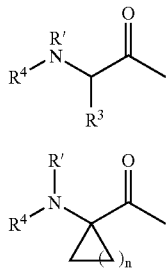

(A)

(B)

wherein, in formula (B), n is an integer from 1 to 5;

$R_2$ is H, $C_{1-6}$alkyl $C_{3-6}$cycloalkyl-$C_{0-6}$alkyl, Ar—$C_{0-6}$alkyl, Het-$C_{0-6}$alkyl, $R_9$(C(O)—, $R_9$C(S)—, $R_9$SO$_2$—, $R_9$OC(O)—, $R_9R_{11}$NC(O)——, $R_9R_{11}$NC(S)——, $R_9(R_{11})$NSO$_2$——,

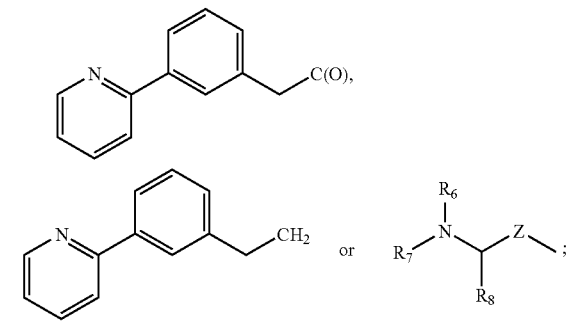

$R_3$ is H, $C_{1-6}$alkyl, $C_{3-6}$cycloalkyl-$C_{0-6}$alkyl, $C_{2-6}$alkenyl, $C_{2-6}$alkynyl, Het$C_{0-6}$alkyl, Ar$C_{0-6}$alkyl, Ar—Ar$C_{0-6}$alkyl, Ar-Het$C_{0-6}$alkyl, Het-Ar$C_{0-6}$alkyl, or Het-Het$C_{0-6}$alkyl;

$R_3$ and R' may be connected to form a pyrrolidine, piperidine or morpholine ring;

$R_4$ is $C_{1-6}$alkyl, $C_{3-6}$cycloalkyl-$C_{0-6}$alkyl, Ar—$C_{0-6}$alkyl, Het-$C_{0-6}$alkyl, $R_5$C(O), $R_5$—C(S)—, $R_5$SO$_2$—, $R_5$OC(O)—, $R_5R_{12}$NC(O)—, or $R_5R_{12}$NC(S)—;

$R_5$ is H, $C_{1-6}$alkyl, $C_{2-6}$alkenyl $C_{2-6}$alkynyl, $C_{3-6}$cycloalkyl-$C_{0-6}$alkyl, $C_{2-6}$alkanonyl, Ar—$C_{0-6}$alkyl, Het-$C_{0-6}$alkyl Ar—Ar$C_{0-6}$alkyl, Ar-Het$C_{0-6}$alkyl, Het-Ar$C_{0-6}$alkyl, or Het-Het$C_{0-6}$alkyl;

$R_6$ is H, $C_{1-6}$alkyl, Ar—$C_{0-6}$alkyl or Het-$C_{0-6}$alkyl;

$R_7$ is H, $C_{1-6}$alkyl, $C_{3-6}$cycloalkyl-$C_{0-6}$alkyl, Ar—$C_{0-6}$alkyl, Het-$C_{0-6}$alkyl, $R_{10}$C(O)—, $R_{10}$C(S)—, $R_{10}$SO$_2$—, $R_{10}$OC(O)—, $R_{10}R_{13}$NC(O)—, or $R_{10}R_{13}$NC(S)—;

$R_8$ is H, $C_{1-6}$alkyl, $C_{2-6}$alkenyl $C_{2-6}$alkynyl, Ar—$C_{0-6}$alkyl or Het-$C_{0-6}$alkyl;

$R_9$ is $C_{1-6}$alkyl, $C_{3-6}$cycloalkyl-$C_{0-6}$alkyl, Aralkyl or Het alkyl;

$R_{10}$ is $C_{1-6}$alkyl, $C_{3-6}$cycloalkyl-$C_{0-6}$alkyl, Ar—$C_{0-6}$alkyl or Het $C_{0-6}$alkyl;

$R_{11}$ is H, $C_{1-6}$alkyl, Ar—$C_{0-6}$alkyl, $C_{3-6}$ cycloalkyl $C_{0-6}$alkyl, or Het-$C_{0-6}$alkyl;

$R_{12}$ is H, $C_{1-6}$alkyl, Ar—$C_{0-6}$alkyl, or Het-$C_{0-6}$alkyl;

$R_{13}$ is H, $C_{1-6}$alkyl, Ar—$C_{0-6}$alkyl, or Het-$C_{0-6}$alkyl;

each $R_{14}$ is independently H, $C_{1-6}$alkyl, OC$_{1-4}$alkyl, SC$_{1-4}$alkyl, N(R$_{12}$)$_2$, CH$_2$OC$_{1-4}$alkyl, CH$_2$SC$_{1-4}$alkyl, CH$_2$N(R$_{12}$)$_2$, Ar—$C_{0-6}$alkyl or Het-$C_{0-6}$alkyl;

R' is H, $C_{1-6}$alkyl, Ar—$C_{0-6}$alkyl, or Het-$C_{0-6}$alkyl;

R" is H, $C_{1-6}$alkyl, Ar—$C_{0-6}$alkyl or Het-$C_{0-6}$alkyl;

Z is C(O) or CH$_2$; or a pharmaceutically acceptable salt, hydrate or solvate thereof.

In another aspect, this invention provides a pharmaceutical composition comprising a compound according to Formula I and a pharmaceutically acceptable carrier, diluent or excipient.

In yet another aspect, this invention provides intermediates useful in the preparation of the compounds of Formula I.

In still another aspect, this invention provides a method of treating diseases in which the disease pathology may be therapeutically modified by inhibiting proteases, particularly cysteine and serine proteases, more particularly cysteine proteases, even more particularly cysteine proteases of the papain superfamily, yet more particularly cysteine proteases of the cathepsin family, most particularly cathepsin K.

In a particular aspect, the compounds of this invention are especially useful for ting diseases characterized by bone loss, such as osteoporosis and gingival diseases, such as gingivitis and periodontitis, or by excessive cartilage or matrix degradation, such as osteoarthritis and rheumatoid arthritis; and for treating certain parasitic diseases, such as malaria.

DETAILED DESCRIPTION

DEFINITIONS AND PREFERRED EMBODIMENTS

The present invention includes all hydrates, solvates, complexes and prodrugs of the compounds of this invention. Prodrugs are any covalently bonded compounds which release the active parent drug according to Formula I in vivo. If a chiral center or another form of an isomeric center is present in a compound of the present invention, all forms of such isomer or isomers, including enantiomers and diastereomers, are intended to be covered herein. Inventive compounds containing a chiral center may be used as a racemic mixture, an enantiomerically enriched mixture, or the racemic mixture may be separated using well-known techniques and an individual enantiomer may be used alone. In cases in which compounds have unsaturated carbon-carbon double bonds, both the cis (Z) and trans (E) isomers are within the scope of this invention. In cases wherein compounds may exist in tautomeric forms, such as keto-enol tautomers, each tautomeric form is contemplated as being included within this invention whether existing in equilibrium or predominantly in one form.

The meaning of any substituent at any one occurrence in Formula I or any subformula thereof is independent of its meaning, or any other substituent's meaning, at any other occurrence, unless specified otherwise.

Abbreviations and symbols commonly used in the peptide and chemical arts are used herein to describe the compounds of the present invention. In general, the amino acid abbreviations follow the IUPAC-IUB Joint Commission on Biochemical Nomenclature as described in Eur. J. Biochem., 158, 9 (1984).

"Proteases" are enzymes that catalyze the cleavage of amide bonds of peptides and proteins by nucleophilic substitution at the amide bond, ultimately resulting in hydrolysis. Such proteases include: cysteine proteases, serine proteases, aspartic proteases, and metalloproteases. The compounds of the present invention are capable of binding more strongly to the enzyme than the substrate and in general are not subject to cleavage after enzyme catalyzed attack by the nucleophile. They therefore competitively prevent proteases from recognizing and hydrolyzing natural substrates and thereby act as inhibitors.

"Hydrogen" or "H" includes all of its possible isotopes, including deuterium and tritium.

"$C_{1-6}$alkyl" as applied herein is meant to include substituted and unsubstituted methyl, ethyl, n-propyl, isopropyl, n-butyl, isobutyl and t-butyl, pentyl, n-pentyl, isopentyl, neopentyl and hexyl and the simple aliphatic isomers thereof. $C_{1-6}$alkyl may be optionally substituted by a moiety selected from the group consisting of: $OR_{15}$, $C(O)R_{15}$, $SR_{15}$, $S(O)R_{15}$, $S(O)_2R_{15}$, $N(R_{15})_2R_{14}NC(O)OR_{16}$, $CO_2R_{15}$, $CO_2N(R_{15})_2$, $N(C=NH)NH_2$, Het, $C_{3-6}$-cycloalkyl, and Ar, where $R_{16}$ is selected from the group consisting of: H, $C_{1-6}$alkyl, $C_{2-6}$-alkenyl, $C_{2-6}$alkynyl, $C_{3-6}$cycloalkyl-$C_{0-6}$alkyl Ar—$C_{0-6}$alkyl and Het-$C_{0-6}$alkyl; and $R_{15}$ is selected from the group consisting of: H, $C_{1-6}$alkyl, Ar—$C_{0-6}$alkyl, and Het $C_{0-6}$alkyl.

"$C_{3-6}$cycloalkyl" as applied herein is meant to include substituted and unsubstituted cyclopropane, cyclobutane, cyclopentane and cyclohexane.

"$C_{2-6}$ alkenyl" as applied herein means an alkyl group of 2 to 6 carbons wherein a carbon-carbon single bond is replaced by a carbon-carbon double bond. $C_{2-6}$alkenyl includes ethylene, 1-propene, 2-propene, 1-butene, 2-butene, isobutene and the several isomeric pentenes and hexenes. Both cis and trans isomers are included.

"$C_{2-6}$alkanonyl" as applied herein is meant to include unsubstituted and substituted acetyl, propanonyl, butanonyl pentanonyl, and hexanonyl "$C_{2-6}$alkynyl" means an alkyl group of 2 to 6 carbons wherein one carbon-carbon single bond is replaced by a carbon-carbon triple bond. $C_{2-6}$ alkynyl includes acetylene, 1-propyne, 2-propyne, 1-butyne, 2-butyne, 3-butyne and the simple isomers of pentyne and hexyne.

"Halogen" means F, Cl, Br, and I.

As used herein "Het" or "heterocyclic" represents a stable 5- to 7-membered monocyclic, a stable 7- to 10-membered bicyclic, or a stable 11- to 18-membered tricyclic heterocyclic ring which is either saturated or unsaturated, and which consists of carbon atoms and from one to three heteroatoms selected from the group consisting of N, O and S, and wherein the nitrogen and sulfur heteroatoms may optionally be oxidized, and the nitrogen heteroatom may optionally be quaternized, and including any bicyclic group in which any of the above-defined heterocyclic rings is fused to a benzene ring. The heterocyclic ring may be attached at any heteroatom or carbon atom which results in the creation of a stable structure, and may optionally be substituted with one or two moieties selected from $C_{0-6}$alkylAr, $C_{1-6}$alkyl, $OR_{17}$, $N(R_{17})_2$, $SR_{17}$, $S(O)R_{15}$, $S(O)_2R_{15}$, $CF_3$, $NO_2$, CN, $CO_2R_{17}$, $CON(R_{17})$, F, Cl, Br and I, where $R_{17}$ is phenyl, naphthyl, or $C_{1-6}$alkyl. Examples of such heterocycles include piperidinyl, piperazinyl, 2-oxopiperazinyl, 2-oxopiperidinyl, 2-oxopyrrolodinyl, 2-oxoazepinyl, azepinyl pyrrolyl, 4-piperidonyl, pyrrolidinyl, pyrazolyl, pyrazolidinyl, imidazolyl, pyridinyl, 1-oxo-pyridinyl, pyrazinyl, oxazolidinyl, oxazolinyl, oxazolyl, isoxazolyl, morpholinyl, thiazolidinyl, thiazolinyl, thiazolyl, quinuclidinyl, indolyl, quinolinyl, quinoxalinyl, isoquinolinyl, benzimidazolyl, benzopyranyl, benzoxazolyl, furanyl, benzofuranyl, thiophenyl, benzo[b]thiophenyl, thieno[3,2-b]thiophenyl, benzo[1,3]dioxolyl, 1,8-naphthyridinyl, pyranyl, tetrahydrofuranyl, tetrahydropyranyl, thienyl, benzoxazolyl, thiamorpholinyl sulfoxide, thiamorpholinyl sulfone, and oxadiazolyl, as well as triazolyl, thiadiazolyl, oxadiazolyl isothiazolyl, imidazolyl, pyridazinyl, pyrimidinyl, triazinyl and tetrazinyl which are available by routine chemical synthesis and are stable. The term heteroatom as applied herein refers to oxygen, nitrogen and sulfur.

"Ar" or "aryl" means phenyl or naphthyl, optionally substituted by one or more of Ph—$C_{0-6}$alkyl; Het-$C_{0-6}$alkyl; $C_{1-6}$alkoxy; Ph—$C_{0-6}$alkoxy; Het-$C_{0-6}$alkoxy; OH, $(CH_2)_{1-6}$ $NR_{15}R_{16}$; $O(CH_2)_{1-6}NR_{15}R_{16}$; $C_{1-6}$alkyl, $OR_{17}$, $N(R_{17})_2$, $SR_{17}$, $S(O)R_{15}$, $S(O)_2R_{15}$, $CF_3$, $NO_2$, CN, $CO_2R_{17}$, $CON(R_{17})$, F, Cl, Br or I; where $R_{15}$ and $R_{16}$ are H, $C_{1-6}$alkyl, Ph—$C_{0-6}$alkyl, naphthyl-$C_{0-6}$alkyl or Het-$C_{0-6}$alkyl; and $R_{17}$ is phenyl, naphthyl, or $C_{1-6}$alkyl.

"Ar—Ar" means aryl covalently linked to a second aryl. Examples of "Ar—Ar" include biphenyl or naphythyl-pheny or phenyl-naphthyl.

"Ar-Het" means an aryl group covalently inked to a heterocycle. Examples of "Ar-Het" include phenyl-piperidine, phenyl-piperazine, phenyl-2-oxopiperazine, naphthyl-piperidine, naphthyl-piperazine, and napthyl-2-oxopiperazine.

"Het-Ar" means a heterocycle covalently linked to a aryl group. Examples of such "Het-Ar" include piperidinyl-phenyl, piperazinyl-phenyl, 2-oxopiperazinyl-phenyl, piperidinyl-naphthyl piperazinyl-naphthyl, and 2-oxopiperazinyl-naphthyl.

"Het-Het" means a heterocycle covalently linked to a second heterocycle. Examples of such "Het-Het" include bipyridine, pyridinyl-piperidine, pyridinyl-piperazine, pyridinyl-2-oxopiperazine, thiophenyl-piperidine, thiophenyl-piperazine, and thiophnyl-2-oxopiperazine.

Here and throughout this application the term $C_0$ denotes the absence of the substituent group immediately following; for instance, in the moiety Ar$C_{0-6}$alkyl, when C is 0, the substituent is Ar, e.g., phenyl. Conversely, when the moiety Ar$C_{0-6}$alkyl is identified as a specific aromatic group, e.g., phenyl, it is understood that the value of C is 0.

Certain radical groups are abbreviated herein. t-Bu refers to the tertiary butyl radical, Boc refers to the t-butyloxycarbonyl radical, Fmoc refers to the fluorenylmethoxycarbonyl radical, Ph refers to the phenyl radical, Cbz refers to the benzyloxycarbonyl radical.

Certain reagents are abbreviated herein. m-CPBA refers to 3-chloroperoxybenzoic acid, EDC refers to N-ethyl-N'-(dimethylaminopropyl)carbodiimide, DMF refers to dimethyl formamide, DMSO refers to dimethyl sulfoxide, TEA refers to triethylamine, TFA refers to trifluoroacetic acid, and THF refers to tetrahydrofuran.

PREFERRED EMBODIMENTS OF THE FORMULAS

In compounds of Formula I, when $R_1$ is

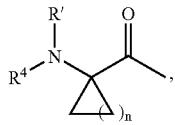

n is preferably 4, to provide 1-amino-1-acyl cyclohexane compounds. The cycloalkyl ring may be unsubstituted or substituted with one or more of $C_{1-6}$alkyl, $C_{3-6}$cycloalkyl-$C_{0-6}$alkyl, $C_{2-6}$alkenyl, $C_{2-6}$alkynyl, HetC$_{0-6}$alkyl, ArC$_{0-6}$alkyl, or halogen.

The cycloalkyl ring is more preferably unsubstituted.

In compounds of Formula I, when $R_1$ is

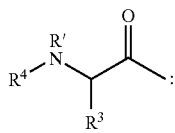

$R_3$ is H, $C_{1-6}$alkyl, $C_{3-6}$ cycloalkyl $C_{0-6}$alkyl, $C_{2-6}$alkenyl, $C_{2-6}$ alkynyl, Het-$C_{0-6}$alkyl, Ar—$C_{0-6}$alkyl, Ar—ArC$_{0-6}$ alkyl, Ar-HetC$_{0-6}$alkyl, Het-ArC$_{0-6}$alkyl, or Het-HetC$_{0-6}$ alkyl.

$R_3$ is preferably H, $C_{3-6}$cycloalkyl-$C_{0-6}$alkyl, Ar—$C_{0-6}$ alkyl, or $C_{1-6}$alkyl.

$R_3$ is more preferably H, methyl, ethyl, n-propyl, prop-2-yl, n-butyl isobutyl, but-2-yl cyclopropylmethyl, cyclohexylmethyl, 2-methanesulfinyl-ethyl, 1-hydroxyethyl, toluyl, naphthalen-2-ylmethyl, benzyloxymethyl, or hydroxymethyl.

$R_3$ is even more preferably toluyl, isobutyl or cyclohexylmethyl.

$R_3$ is most preferably isobutyl.

$R_4$ is H, $C_{1-6}$alkyl, $C_{3-6}$cycloalkyl-$C_{0-6}$alkyl, Ar—$C_{0-6}$ alkyl, Het-$C_{0-6}$alkyl, $R_5C(O)$—, $R_5C(S)$—, $R_5SO_2$—, $R_5OC(O)$—, $R_5R_{12}NC(O)$—, or $R_5R_{12}NC(S)$—.

$R_4$ is more preferably $R_5OC(O)$—, $R_5C(O)$— or $R_5SO_2$—.

$R_4$ is most preferably $R_5C(O)$—.

In some embodiments, $R_4$ is preferably methanesulfonyl.

Preferably $R_5$ is $C_{1-6}$alkyl, $C_{2-6}$alkenyl, $C_{3-6}$cycloalkyl 1, $C_{2-6}$alkanonyl, Ar—$C_{0-6}$alkyl or Het-$C_{0-6}$alkyl.

More preferably, and especially when $R_4$ is $R_5C(O)$—, where $R_5$ is methyl, especially halogenated methyl, more especially trifluoromethyl, especially $C_{1-6}$alkoxy and aryloxy substituted methyl, more especially phenoxy-methyl, 4-fluoro-phenoxy-methyl, especially heterocycle substituted methyl more especially 2-thiophenyl-methyl;

butyl, especially aryl substituted butyl, more especially 4-(4-methoxy)phenyl-butyl;

isopentyl;

cyclohexyl;

pentanonyl, especially 4-pentanonyl;

butenyl, especially aryl substituted butenyl, more especially 4,4-bis(4-ethoxyphenyl)but-3-enyl;

phenyl, especially phenyl substituted with one or more halogens, more especially 3,4-dichlorophenyl and 4-fluorophenyl, especially phenyl substituted with one or more $C_{1-6}$ alkoxy or aryloxy groups, more especially 3,4-dimethoxy-phenyl, 3-benzyloxy-4-methoxy-phenyl, especially phenyl substituted with one or more sulfonyl groups, more especially 4methanesulfonyl-phenyl;

benzyl;

naphthalenyl, especially naphthylen-2-yl;

benzo[1,3]dioxolyl, especially benzo[1,3]dioxol-5-yl, furanyl, especially furan-2-yl, especially substituted furanyl, such as 5-nitro-furan-2-yl, 5-(4-nitrophenyl)-furan-2-yl, 5-(3-trifluoromethyl-phenyl)furan-2-yl, more especially halogen substituted furanyl, even more especially 5-bromo-furan-2-yl, more especially aryl substituted furanyl, even more especially 5-(chloro-phenyl)-furan-2-yl;

tetrahydrofuranyl, especially tetrahydrofuran-2-yl;

benzofuranyl, especially benzofuran-2-yl, and especially $C_{1-6}$alkoxy substituted benzofuranyl, more especially 5-(2-piperazin-4-carboxylic acid tert-butyl ester-ethoxy) benzofuran-2-yl, 5-(2-morpholino-4-yl-ethoxy)benzofuran-2-yl, 5-(2-piperazin-1-yl-ethoxy)benzofuran-2-yl, 5-(2-cyclohexyl-ethoxy)-benzofuran-2-yl; 7-methoxybenzofuran-2-yl, 5-methoxy-benzofura-2-yl, 5,6 dimethoxy-benzofuran-2-yl, especially halogen substituted benzofuranyl, more especially 5-fluoro-benzofuran-2-yl, 5,6-difluoro-benzofuran-2-yl, especially $C_{1-6}$alkyl substituted benzofuranyl, most especially 3-methyl-benzofuran-2-yl;

benzo[b]thiophenyl, especially benzo[b]thiophen-2-yl; especially $C_{1-6}$alkoxy substituted benzo[b]thiophenyl, more especially 5, dimethoxy-benzo[b]thiophen-2-yl;

quinolinyl, especially quinolin-2-yl, quinolin-3-yl, quinolinyl, quinolinyl, or quinolin-8-yl;

quinoxalinyl, especially quinoxalin-2-yl;

1,8-naphthyridinyl, especially 1,8-naphthyridin-2-yl;

indolyl, especially indol-2-yl, especially indol-6-yl, indol-5-yl, especially $C_{1-6}$alkyl substituted indolyl, more especially N-methyl-indol-2-yl;

pyridinyl, especially pyridin-2-yl, pyridin-5-yl, especially 1-oxy-pyridin-2-yl, especially $C_{1-6}$alkyl substituted pyridinyl, more especially 2-methyl-pyridin-5-yl;

furo[3,2-b]pyridinyl, especially furo[3,2-b]pyridin-2-yl, and $C_{1-6}$alkyl substituted furo[3,2-b]pyridinyl, especially 3-methyl-furo[3,2-b]pyridin-2-yl;

thiophenyl especially thiophen-3-yl, especially $C_{1-6}$alkyl substituted thiophenyl, more especially 5-methyl-thiophen-2-yl, especially halogen substituted thiophenyl, more especially 4,5&bromo-thiophen-2-yl;

thieno[3,2-b]thiophene, especially thieno[3,2-b]thiophene-2-yl, more especially $C_{1-6}$alkyl substituted thieno[3,b]thiophene-2-yl, more especially 5-tert-butyl-3-methyl-thieno[3,2-b]thiophene-2-yl;

isoxazolyl, especially isoxazol-4-yl, especially $C_{1-6}$alkyl substituted isoxazolyl, more especially 3,5-dimethyl-isoxazol-4-yl;

oxazolyl, especially oxazol-4-yl, more especially 5-methyl-2-phenyl oxazol-4-yl, or 2-phenyl-5-trifluoromethyl-oxazol-4-yl.

When $R_4$ is $R_5SO_2$, $R_5$ is preferably pyridin-2-yl or 1-oxo-pyridin-2-yl.

R' is preferably H or naphthalen-2-yl-methyl. Most preferably R' is H.

R" is most preferably H or $C_{1-6}$alkyl.

$R_{14}$ is most preferably H, $C_{1-6}$alkyl, especially is methyl, ethyl propyl, butyl, pentyl or hexyl, more especially methyl.

Preferably $R_2$ is $C_{1-6}$alkyl, $C_{3-6}$cycloalkyl $C_{0-6}$alkyl, Ar—$C_{0-6}$alkyl, $R_9C(O)$—, $R_9SO_2$, $R_9R_{11}NC(O)$—, or

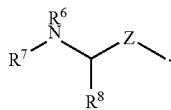

More preferably $R_2$ is $C_{1-6}$alkyl, $C_{3-6}$ cycloalkyl-$C_{0-6}$-alkyl, Ar—$C_{0-6}$alkyl. Most preferably $R_2$ is $R_9SO_2$ or $C_{3-6}$cycloalkyl-$C_{0-6}$alkyl.

In such embodiments $R_6$ is preferably H, $C_{1-6}$alkyl, Ar—$C_{1-6}$alkyl, or Het-$C_{0-6}$alkyl; more preferably H.

In addition, in such embodiments, $R_7$ is preferably $R_9$OC(O); $R_8$ is preferably $C_{1-6}$alkyl, more preferably isobutyl; and $R_9$ is $C_{1-6}$alkyl, $C_{3-6}$cycloalkyl-$C_{0-6}$alkyl, Ar—$C_{0-6}$alkyl, and Het-$C_{0-9}$alkyl.

More preferably, in such embodiments, $R_9$ is methyl; ethyl, especially $C_{1-6}$alkyl-substituted ethyl more especially 2-cyclohexyl-ethyl; butyl, especially $C_{1-6}$butyl, more especially 3-methylbutyl; tert-butyl, particularly when $R_2$ is $R_9$OC(O); isopentyl; phenyl, especially halogen substituted phenyl, more especially 3,4-dichlorophenyl, 4-bromophenyl, 2-fluorophenyl, 4-fluorophenyl, 3-chlorophenyl, chlorophenyl, especially $C_{1-6}$alkoxy phenyl, more especially 3-methoxyphenyl, 4-methoxyphenyl, 3,4 dimethoxyphenyl, especially cyanophenyl, more especially 2-cyanophenyl; toluyl, especially Het-substituted toluyl, more especially 3-(pyridin-2-yl)toluyl; naphthylenyl, especially naphthylen-2-yl; benzoyl, especially 2-benzoyl; benzo[1,3]dioxolyl, especially benzo[1,3]dioxol-5-yl; benzo[1,2,5]oxadiazolyl, especially benzo[1,2,5]oxadiazol-4-yl; pyridinyl, especially pyridin-2-yl, pyridin-3-yl, especially 1-oxy-pyridinyl, more especially 1-oxy-pyridin-2-yl, 1-oxy-pyridin-3-yl; especially $C_{1-6}$alkylpyridinyl, more especially 3-methyl-pyridin-2-yl, 6-methyl-pyridin-2-yl, thiophene, especially thiophene-2-yl; thiazolyl, especially thiazol-2-yl; 1H-imidazolyl, especially 1H-imidazol-2-yl, 1H-imidazolyl, more especially $C_{1-6}$alkyl substituted imidazolyl, even more especially 1-methyl-1H-imidazol-2-yl, 1-methyl-1H-imidazolyl; 1H-[1,2,4]triazolyl, especially 1H-[1,2,4]triazol-3-yl, more especially $C_{1-6}$alkyl substituted 1H-[1,2,4]triazolyl, even more especially 5-methyl-1H-[1,2,4]triazol-3-yl; or quinolinyl.

When $R_2$ is $R_9SO_2$, $R_9$ is most preferably pyridin-2-yl or 1-xy-pyridin-2-yl; and $R_{10}$ is preferably $C_{1-6}$alkyl, Ar—$C_{0-6}$alkyl or Het-$C_{0-6}$alkyl.

Z is preferably C(O) or $CH_2$.

$R_2$ is also preferably H, cyclohexyl, methylcyclohexyl, toluyl, aryl substituted ethyl, especially 2-phenyl ethyl, or 2-[3-(pyridin-2-yl) phenyl]ethyl.

Compounds of Formula I where R" is H are preferred.

More preferred are compounds of Formula I wherein:
$R_1$ is

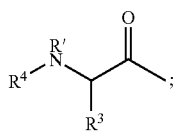

where:
$R_2$ is as defined above;
$R_3$ is H, $C_{1-6}$, $C_{3-6}$cycloalkyl k, or Ar—$C_{0-6}$alkyl;
$R_4$ is $R_5C(O)$—, $R_{14}SO_2$—, or $R_5OC(O)$—;

$R_5$ is $C_{1-6}$alkyl, $C_{2-6}$alkenyl, $C_{3-6}$cycloalkyl-$C_{0-6}$alkyl, $C_{2-6}$alkanonyl, Ar—$C_{0-6}$alkyl or Het-$C_{0-6}$alkyl;

$R_6$ is H, $C_{1-6}$alkyl, Ar—$C_{0-6}$alkyl, or Het-$C_{0-6}$alkyl;

$R_7$ is H, $C_{1-6}$alkyl, $C_{3-6}$cycloalkyl-$C_{0-6}$alkyl, Ar—$C_{0-6}$alkyl, Het-$C_{0-6}$alkyl, $R_{10}C(O)$—;

$R_8$ is H, $C_{1-6}$alkyl, $C_{2-6}$alkenyl, $C_{2-6}$alkynyl, Het-$C_{0-6}$alkyl or Ar—$C_{0-6}$alkyl;

$R_9$ is $C_{1-6}$alkyl, $C_{3-6}$cycloalkyl-$C_{0-6}$alkyl, Ar—$C_{0-6}$alkyl or Het-$C_{0-6}$alkyl;

$R_{10}$ is $C_{1-6}$alkyl, $C_{3-6}$cycloalkyl-$C_{0-6}$alkyl, Ar—$C_{0-6}$alkyl or Het-$_{0-6}$ alkyl;

$R_{11}$ is H, $C_{1-6}$alkyl, Ar—$C_{1-6}$alkyl, $C_{3-6}$cycloalkyl-$C_{0-6}$alkyl, or Het-$C_{0-6}$alkyl;

$R_{12}$ is H, $C_{1-6}$alkyl, Ar—$C_{0-6}$alkyl, or Het-$C_{0-6}$alkyl;

$R_{13}$ is H, $C_{1-6}$alkyl, Aryl, or Het-$C_{0-6}$alkyl;

each $R_{14}$ is independently H, $C_{1-6}$alkyl, $C_{2-6}$ alkenyl, $C_{3-6}$cycloalkyl $C_{0-6}$alkyl, $C_{2-6}$alkanonyl, Ar—$C_{0-6}$alkyl or Het-$C_{0-6}$alkyl;

R' is H; and
R" is H.

Particularly preferred are such compounds wherein $R_3$ is isobutyl.

Still more preferred are compounds of Formula I wherein:
$R_1$ is

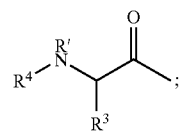

$R_2$ is H, $C_{3-6}$cycloalkyl-$C_{0-6}$alkyl, Ar—$C_{0-6}$alkyl, $R_9C(O)$—, $R_9SO_2$, $R_9R_{11}NC(O)$—, or

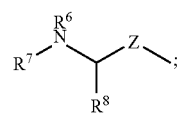

$R_3$ is H, $C_{1-6}$alkyl, $C_{3-6}$cycloalkyl-$C_{0-6}$alkyl or Ar—$C_{0-6}$alkyl;

$R_4$ is $R_5OC(O)$—, $R_5C(O)$— and $R_5SO_2$;

$R_5$ is $C_{1-6}$alkyl, $C_{2-6}$alkenyl, $C_{3-6}$cycloalkyl-$C_{0-6}$alkanonyl, Ar—$C_{0-6}$alkyl or Het-$C_{0-6}$alkyl;

$R_6$ is H;

$R_7$ is $R_{10}OC(O)$;

$R_8$ is $C_1$ alkyl;

$R_9$ is $C_{1-6}$alkyl, $C_{3-6}$cycloalkyl-$C_{0-6}$alkyl, Ar—$C_{0-6}$alkyl or Het-$C_{0-6}$alkyl;

$R_{10}$ is $C_{1-6}$alkyl, Ar—$C_{0-6}$alkyl or Het-$C_{0-6}$alkyl;

$R_{11}$ is $C_{1-6}$alkyl, $C_{3-6}$cycloalkyl $C_{0-6}$alkyl Ar—$C_{0-6}$alkyl or Het-$C_{0-6}$alkyl;

R' is H; and
R" is H;

Even more preferred are such compounds of Formula I wherein $R_2$ is Ar—$C_{0-6}$alkyl, $R_9C(O)$—, or $R_9SO_2$.

Yet more preferred are compounds of Formula I wherein:

$R_1$ is

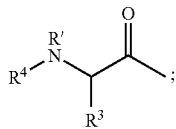

$R_2$ is $C_{3-6}$cycloalkyl-$C_{0-6}$alkyl, or Ar—$C_{0-6}$alkyl;

$R_3$ is H, methyl, ethyl, n-propyl, prop-2-yl, n-butyl, isobutyl, but-2-yl, cyclopropylmethyl, cyclohexylmethyl, 2-methanesulfinyl-ethyl, 1-hydroxyethyl, toluyl, naphthalen-2-ylmethyl, benzyloxymethyl or hydroxymethyl;

$R_4$ is $R_5C(O)$—;

$R_5$ is hydrogen, methyl, especially halogenated methyl, more especially trifluoromethyl, especially $C_{1-6}$alkoxy and aryloxy substituted methyl, more especially phenoxy-methyl, 4-fluoro-phenoxy-methyl, especially heterocycle substituted methyl, more especially 2-thiophenyl-methyl; butyl, especially aryl substituted butyl, more especially 4-(4-methoxy)phenyl-butyl; isopentyl; cyclohexyl; pentanonyl, especially 4-pentanonyl; butenyl, especially aryl substituted butenyl, more especially 4,4-bis(4-methoxyphenyl)-but-3-enyl; phenyl, especially phenyl substituted with one or more halogens, more especially 3,4-dichlorophenyl and 4-fluorophenyl, especially phenyl substituted with one or more $C_{1-6}$alkoxy or aryloxy groups, more especially 3,4-dimethoxy-phenyl, 3-benzyloxy methoxy-phenyl, especially phenyl substituted with one or more sulfonyl groups, more especially 4-methanesulfonyl-phenyl; benzyl; naphthylen-2-yl; benzo[1,3]dioxolyl, especially benzo[1,3]dioxol-5-yl; furanyl especially furan-2-yl, especially substituted furanyl, such as 5-nitro-furan-2-yl, 5-(4-nitrophenyl)furan-2-yl 5(3-trifluoromethyl-phenyl)furan-2-yl, more especially halogen substituted furanyl, even more especially 5-bromo-furan-2-yl, more especially aryl substituted furanyl, even more especially 5-(4-chloro-phenyl)furan-2-yl; tetrahydrofuran-2-yl; benzofuranyl, especially benzofuran-2-yl, and especially $C_{1-6}$alkoxy substituted benzofuranyl, more especially 52-piperazin-4-carboxylic acid tert-butyl ester-ethoxy) benzofuran-2-yl, 5-morpholino-4-ethoxy)-benzofuran-2-yl, 52-piperazin-1-yl-ethoxy)benzofuran-2-yl, 52-cyclohexyl-ethoxy)-benzofuran-2-yl, 7-methoxy-benzofuran-2-yl, 5-methoxy-benzofuran-2-yl, 5,6-dimethoxy-benzofuran-2-yl, especially halogen substituted benzofuranyl, more especially 5-fluoro-benzofuran-2-yl, 5,6-difluoro-benzofuran-2-yl, especially $C_{1-6}$alkyl substituted benzofuranyl, most especially 3-methyl-benzofuran-2-yl; benzo[b]thiophenyl, especially benzo[b]thiophen-2-yl; especially $C_{1-6}$alkoxy substituted benzo[b]thiophenyl, more especially 5,6-dimethoxy-benzo[b]thiophen-2-yl; quinolinyl, especially quinolin-2-yl quinolin-3-yl, quinolin-4-yl, quinolinyl, and quinolin-8-yl; quinoxalinyl, especially quinoxalin-2-yl; 1,8-naphthyridinyl, especially 1,8-naphthyridin-2-yl; indolyl, especially indol-2-yl, especially indol-6-yl, indol-5-yl, especially $C_{1-6}$alkyl substituted indolyl, more especially N-methyl-indol-2-yl; pyridinyl, especially pyridin-2-yl, pyridin-5-yl, especially 1-oxy-pyridin-2-yl, especially $C_{1-6}$alkyl substituted pyridinyl more especially 2-methyl-pyridin-5-yl; furo[3,2-b]pyridinyl, especially furo[3,2-b]pyridin-2-yl, and $C_{1-6}$alkyl substituted furo[3,2-b]pyridinyl, especially 3-methyl-furo[3,2b]pyridin-2-yl; thiophenyl, especially thiophen-3-yl, especially $C_{1-6}$alkyl substituted thiophenyl, more especially 5-methyl-thiophen-2-yl, especially halogen substituted thiophenyl, more especially 4,5-dibromo-thiophen-2-yl; thieno[3,2-b]thiophene, especially thieno[3,2-b]thiophene-2-yl, more especially $C_{1-6}$alkyl substituted thieno[3,2-b]thiophene-2-yl, more especially 5-tert-butyl-3-methyl-thieno[3,2-b]thiophene-2-yl; isoxazolyl, especially isoxazolyl, especially $C_{1-6}$alkyl substituted isoxazolyl, more especially 3,5-dimethyl-isoxazolyl; or oxazolyl, especially oxazolyl, more especially 5-methyl-2-phenyl oxazolyl, 2-phenyl-5-trifluoromethyl-oxazolyl;

$R_9$ is methyl; ethyl, especially $C_{1-6}$alkyl-substituted ethyl, more especially 2-cyclohexyl-ethyl; butyl, especially $C_{1-6}$butyl, more especially 3-methylbutyl; tert-butyl, particularly when $R_2$ is $R_9OC(O)$; isopentyl; phenyl especially halogen substituted phenyl, more especially 3,4-dichlorophenyl, 4-bromophenyl, 2-fluorophenyl, 4-fluorophenyl, 3-chlorophenyl, 4-chlorophenyl, especially $C_{1-6}$alkoxy phenyl, more especially 3-methoxyphenyl, 4-methoxyphenyl, 3,4-dimethoxyphenyl, especially cyanophenyl, more especially 2-cyanophenyl; toluyl, especially Het-substituted toluyl, more especially 3-(pyridin-2-yl)toluyl; naphthylene, especially naphthyl-2-ene; benzoyl, especially 2-benzoyl; benzo[1,3]dioxolyl, especially benzo[1,3]dioxol-5-yl; benzo[1,2,5]oxadiazolyl, especially benzo[1,2,5]oxadiazolyl; pyridinyl, especially pyridin-2-yl, pyridin-3-yl, especially 1-oxy-pyridinyl, more especially 1-oxy-pyridin-2-yl, 1-oxy-pyridin-3-yl; especially $C_{1-6}$alkylpyridinyl, more especially 3-methyl-pyridin-2-yl, 6-methyl-pyridin-2-yl, thiophenyl, especially thiophene-2-yl; thiazolyl, especially thiazol-2-yl; 1H-imidazolyl, especially 1H-imidazol-2-yl, 1H-imidazol-1-yl, more especially $C_{1-6}$alkyl substituted imidazolyl, even more especially 1-methyl-1H-imidazol-2-yl, 1-methyl-1H-imidazol yl; 1H-[1,2,4]triazolyl, especially 1H-[1,2,4]triazol-3-yl, more especially $C_{1-6}$alkyl substituted 1H-[1,2,4]triazolyl, even more especially 5-methyl-1H-[1,2,4]triazol-3-yl; or quinolinyl; and;

R' is H.

Even yet more preferred are compounds of Formula I wherein:

$R_1$ is

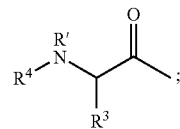

$R_2$ is $C_{3-6}$cycloalkyl-$C_{0-6}$alkyl or $R_9SO_2$;

$R_3$ is $C_{1-6}$alkyl;

$R_4$ is $R_5C(O)$;

$R_5$ is Het-$C_{0-6}$alkyl;

$R_9$ is Het-$C_{0-6}$alkyl;

R' is H; and

R" is H

Still yet more preferred are compounds of Formula I wherein:

$R_1$ is

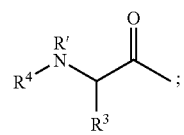

$R_2$ is $C_{3-6}$cycloalkyl-$C_{0-6}$alkyl;
$R_3$ is isobutyl;
$R_4$ is $R_5C(O)$;
$R_5$ is hydrogen, 5-methoxybenzofuran-2-yl, benzo[b]thiophen-2-yl, 3-methylbenzofuran-2-yl, thieno[3,2-b]thiophen-2-yl, benzofuran-2-yl, furo[3,2-b]pyridin-2-yl, 3-methyl-furo[3,2-b]pyridin-2-yl; preferably benzofuran-2-yl, furo[3,2-b]pyridin-2-yl, or 3-methyl-furo[3,2-b]pyridin-2-yl; most preferably benzofuran-2-yl.
$R_9$ is pyridin-2-yl or 1-oxy-pyridin-2-yl, preferably pyridin-2-yl.
R' is H; and
R" is H.

Synthetic Methods

Synthetic methods to prepare the compounds of this invention frequently employ protective groups to mask a reactive functionality or minimize unwanted side reactions. Such protective groups are described generally in Green, T. W, PROTECTIVE GROUPS IN ORGANIC SYNTHESIS, John Wiley & Sons, New York (1981). The term "amino protecting groups" generally refers to the Boc, acetyl, benzoyl, Fmoc and Cbz groups and derivatives thereof as known to the art. Methods for protection and deprotection, and replacement of an amino protecting group with another moiety are well known.

Acid addition salts of the compounds of Formula I are prepared in a standard manner in a suitable solvent from the parent compound and an excess of an acid, such as hydrochloric, hydrobromic, hydrofluoric, sulfuric, phosphoric, acetic, trifluoroacetic, maleic, succinic or methanesulfonic. Certain of the compounds form inner salts or zwitterions which may be acceptable. Cationic salts are prepared by treating the parent compound with an excess of an alkaline reagent, such as a hydroxide, carbonate or alkoxide, containing the appropriate cation; or with an appropriate organic amine. Cations such as $Li^+$, $Na^+$, $K^+$, $Ca^{++}$, $Mg^+$ and $NH_4^+$ are specific examples of cations present in pharmaceutically acceptable salts. Halides, sulfates, phosphates, alkanoates (such as acetate and trifluoroacetate), benzoates, and sulfonates (such as mesylate) are examples of anions present in pharmaceutically acceptable salts.

This invention also provides a pharmaceutical composition which comprises a compound according to Formula I and a pharmaceutically acceptable carrier, diluent or excipient. Accordingly, the compounds of Formula I may be used in the manufacture of a medicament. Pharmaceutical compositions of the compounds of Formula I prepared as hereinbefore described may be formulated as solutions or lyophilized powders for parenteral administration. Powders may be reconstituted by addition of a suitable diluent or other pharmaceutically acceptable carrier prior to use. The liquid formulation may be a buffered, isotonic, aqueous solution. Examples of suitable diluents are normal isotonic saline solution, standard 5% dextrose in water or buffered sodium or ammonium acetate solution. Such formulation is especially suitable for parenteral administration, but may also be used for oral administration or contained in a metered dose inhaler or nebulizer for insufflation. It may be desirable to add excipients such as polyvinylpyrrolidone, gelatin, hydroxy cellulose, acacia, polyethylene glycol mannitol, sodium chloride or sodium citrate.

Alternately, these compounds may be encapsulated, tableted or prepared in an emulsion or syrup for oral administration. Pharmaceutically acceptable solid or liquid carriers may be added to enhance or stabilize the composition, or to facilitate preparation of the composition. Solid carriers include starch, lactose, calcium sulfa dihydrate, terra alba, magnesium stearate or stearic acid, talc, pectin, acacia, agar or gelatin. Liquid carriers include syrup, peanut oil, olive oil, saline and water. The carrier may also include a sustained release material such as glyceryl monostearate or glyceryl distearate, alone or with a wax. The amount of solid carrier varies but, preferably, will be between about 20 mg to about 1 g per dosage unit. The pharmaceutical preparations are made following the conventional techniques of pharmacy involving milling, mixing, granulating, and compressing, when necessary, for tablet forms; or milling, mixing and filling for hard gelatin capsule forms. When a liquid carrier is used, the preparation will be in the form of a syrup, elixir, emulsion or an aqueous or non-aqueous suspension. Such a liquid formulation may be administered directly p.o. or filled into a soft gelatin capsule.

For rectal administration, the compounds of this invention may also be combined with excipients such as cocoa butter, glycerin, gelatin or polyethylene glycols and molded into a suppository.

Utility of the Invention

The compounds of Formula I are useful as protease inhibitors, particularly as inhibitors of cysteine and serine proteases, more particularly as inhibitors of cysteine proteases, even more particularly as inhibitors of cysteine proteases of the papain superfamily, yet more particularly as inhibitors of cysteine proteases of the cathepsin family, most particularly as inhibitors of cathepsin K. The present invention also provides useful compositions and formulations of said compounds, including pharmaceutical compositions and formulations of said compounds.

The present compounds are useful for treating diseases in which cysteine proteases are implicated, including infections by *pneumocystis carinii, trypsanoma cruzi, trypsanoma brucei*, and *Crithidia fusiculata*; as well as in schistosomiasis, malaria, tumor metastasis, metachromatic leukodystrophy, muscular dystrophy, amytrophy; and especially diseases in which cathepsin K is implicated, most particularly diseases of excessive bone or cartilage loss, including osteoporosis, gingival disease including gingivitis and periodontitis, arthritis, more specifically, osteoarthritis and rheumatoid arthritis, Paget's disease; hypercalcemia of malignancy, and metabolic bone disease.

Parasites known to utilize cysteine proteases in their life cycle (and the diseases caused by these parasites) include *Trypanosoma cruzi, Trypanosoma Brucei* [trypanosomiasis (African sleeping sickness, Chagas disease)], *Leishmania mexicana,—Leishmania pifanoi, Leishmania major* (leishmaniasis), *Schistosoma mansoni* (schistosomiasis), *Onchocerca volvulus* [onchocerciasis (river blindness)] *Brugia pahangi, Entamoeba histolytica, Giardia lambia*, the helminths, *Haemonchus contortus* and *Fasciola hepatica*, as well as helminths of the genera *Spirometra, Trichinella,— Necator* and *Ascaris*, and protozoa of the genera *Cryptosporidium, Eimeria,—Toxoplasma* and *Naegleria*. The compounds of the present invention are suitable for treating diseases caused by these parasites which may be therapeutically modified by altering the activity of cysteine proteases. In particular, the present compounds are useful for treating malaria by inhibiting falcipain.

Metastatic neoplastic cells also typically express high levels of proteolytic enzymes that degrade the surrounding matrix, and certain tumors and metastatic neoplasias may be effectively treated with the compounds of this invention.

The present invention also provides methods of treatment of diseases caused by pathological levels of proteases, particularly cysteine and serine proteases, more particularly cysteine proteases, even more particularly cysteine proteases of the papain superfamily, yet more particularly cysteine proteases of the cathepsin family, which methods comprise administering to an animal, particularly a mammal, most particularly a human in need thereof a compound of the present invention. The present invention especially provides methods of treatment of diseases caused by pathological levels of cathepsin K, which methods comprise administering to an animal, particularly a mammal, most particularly a human in need thereof an inhibitor of cathepsin K, including a compound of the present invention. The present invention particularly provides methods for treating diseases in which cysteine proteases are implicated, including infections by *pneumocystis carinii, trypsanoma cruzi, trypsanoma brucei*, and *Crithidia fusiculata*; as well as in schistosomiasis, malaria, tumor metastasis, metachromatic leukodystrophy, muscular dystrophy, amytrophy, and especially diseases in which cathepsin K is implicated, most particularly diseases of excessive bone or cartilage loss, including osteoporosis, gingival disease including gingivitis and periodontitis, arthritis, more specifically, osteoarthritis and rheumatoid arthritis, Paget's disease, hypercalcemia of malignancy, and metabolic bone disease.

The present method provides treatment of diseases (in parentheses) caused by infection by *Trypanosoma cruzi, Trypanosoma Brucei* [trypanosomiasis (African sleeping sickness, Chagas disease)], *Leishmania mexicana, Leishmania pifanoi,—Leishmania major* (leishmaniasis), *Schistosoma mansoni* (schistosomiasis), *Onchocerca volvulus* [onchocerciasis (river blindness)] *Brugia pahangi, Entamoeba histolytica,—Giardia lambia,* the helminths, *Haemonchus contortus* and *Fasciola hepatica*, as well as helminths of the genera *Spirometra, Trichinella, Necator* and *Ascaris*, and protozoa of the genera *Cryptosporidium, Eimeria, Toxoplasma* and *Naegleria* by inhibiting cysteine proteases of the papain superfamily by administering to a patient in need thereof, particularly an animal, more particularly a mammal, most particularly a human being, one or more of the above-listed compounds.

Most particularly, the present invention provides a method of treating malaria, caused by infection with *Plasmodium falciparum*, by the inhibition of falcipain by administering to a patient in need thereof, particularly an animal, more particularly a mammal, most particularly a human being, one or more of the above-listed compounds.

The present method may be practiced by administering the above-listed compounds alone or in combination, with each other, or with other therapeutically effective compounds.

This invention further provides a method for treating osteoporosis or inhibiting bone loss which comprises internal administration to a patient of an effective amount of a compound of Formula I, alone or in combination with other inhibitors of bone resorption, such as bisphosphonates (i.e., allendronate), hormone replacement therapy, anti-estrogens, or calcitonin. In addition, treatment with a compound of this invention and an anabolic agent, such as bone morphogenic protein, iproflavone, may be used to prevent bone loss or to increase bone mass.

For acute therapy, parenteral administration of a compound of Formula I is preferred. An intravenous infusion of the compound in 5% dextrose in water or normal saline, or a similar formulation with suitable excipients, is most effective, although an intramuscular bolus injection is also useful. Typically, the parenteral dose will be about 0.01 to about 100 mg/kg; preferably between 0.1 and 20 mg/kg, in a manner to maintain the concentration of drug in the plasma at a concentration effective to inhibit cathepsin K. The compounds are administered one to four times daily at a level to achieve a total daily dose of about 0.4 to about 400 mg/kg/day. The precise amount of an inventive compound which is therapeutically effective, and the route by which such compound is best administered, is readily determined by one of ordinary skill in the art by comparing the blood level of the agent to the concentration required to have a therapeutic effect.

The compounds of this invention may also be administered orally to the patient, in a manner such that the concentration of drug is sufficient to inhibit bone resorption or to achieve any other therapeutic indication as disclosed herein. Typically, a pharmaceutical composition containing the compound is administered at an oral dose of between about 0.1 to about 50 mg/kg in a manner consistent with the condition of the patient. Preferably the oral dose would be about 05 to about 20 mg/kg.

No unacceptable toxicological effects are expected when compounds of the present invention are administered in accordance with the present invention.

Bioassay

The compounds of this invention may be tested in one of several biological assays to determine the concentration of compound which is required to have a given pharmacological effect.

Determination of Cathepsin K Proteolytic Catalytic Activity

All assays for cathepsin K were carried out with human recombinant enzyme. Standard assay conditions for the determination of kinetic constants used a fluorogenic peptide substrate, typically Cbz-Phe-Arg-AMC, and were determined in 100 mM Na acetate at pH 55 containing 20 mM cysteine and 5 nM EDTA. Stock substrate solutions were prepared at concentrations of 10 or 20 mM in DMSO with 20 uM final substrate concentration in the assays. All assays contained 10% DMSO. Independent experiments found that this level of DMSO had no effect on enzyme activity or kinetic constants. All assays were conducted at ambient temperature. Product fluorescence (excitation at 360 nM; emission at 460 nM) was monitored with a Perceptive Biosystems Cytofluor II fluorescent plate reader. Product progress curves were generated over 20 to 30 minutes following formation of AMC product.

Inhibition Studies

Potential inhibitors were evaluated using the progress curve method. Assays were carried out in the presence of variable concentrations of test compound. Reactions were initiated by addition of enzyme to buffered solutions of inhibitor and substrate. Data analysis was conducted according to one of two procedures depending on the appearance of the progress curves in the presence of inhibitors. For those compounds whose progress curves were linear, apparent inhibition constants ($K_{i,app}$) were calculated according to equation 1 (Brandt et ale Biochemitsry, 1989, 28, 140):

$$v=V_m A/[K_a(1+I/K_{i,app})+A] \qquad (1)$$

where v is the velocity of the reaction with maximal velocity $V_m$, A is the concentration of substrate with Michaelis constant of $K_a$, and I is the concentration of inhibitor.

For those compounds whose progress curves showed downward curvature characteristic of time-dependent inhibition, the data from individual sets was analyzed to give $k_{obs}$ according to equation 2:

$$[AMC] = v_{ss}t + (v_0 - v_{ss})[1 - \exp(-k_{obs}t)]/k_{obs} \quad (2)$$

where [AMC] is the concentration of product formed over time t, $v_0$ is the initial reaction velocity and $v_{ss}$ is the final steady state rate. Values for $k_{obs}$ were then analyzed as a linear function of inhibitor concentration to generate an apparent second order rate constant $k_{obs}$/inhibitor concentration or kobs/[T]) describing the time-dependent inhibition. A complete discussion of this kinetic treatment has been fully described (Morrison et al., Adv. Enzymol. Relat. Areas Mol. Biol., 1988, 61, 201).

Human Osteoclast Resorption Assay

Aliquots of osteoclastoma-derived cell suspensions were removed from liquid nitrogen storage, warmed rapidly at 37° C. and washed ×1 in RPMI-1640 medium by centrifugation (1000 rpm, 5 min at 4° C.). The medium was aspirated and replaced with murine anti-HLA-DR antibody, diluted 1:3 in RPMI-1640 medium, and incubated for 30 min on ice The cell suspension was mixed frequently.

The cells were washed ×2 with cold RPMI-1640 by centrifugation (1000 rpm, 5 min at 4° C.) and then transferred to a sterile 15 mL centrifuge tube. The number of mononuclear cells were enumerated in an improved Neubauer counting chamber.

Sufficient magnetic beads (5/mononuclear cell), coated with goat anti-mouse IgG, were removed from their stock bottle and placed into 5 mL of fresh medium (this washes away the toxic azide preservative). The medium was removed by immobilizing the beads on a magnet and is replaced with fresh medium.

The beads were mixed with the cells and the suspension was incubated for 30 min on ice. The suspension was mixed frequently. The bead-coated cells were immobilized on a magnet and the remaining cells (osteoclast-rich fraction) were decanted into a sterile 50 mL centrifuge tube. Fresh medium was added to the bead-coated cells to dislodge any trapped osteoclasts. This wash process was repeated ×10. The bead-coated cells were discarded.

The osteoclasts were enumerated in a counting chamber, using a large-bore disposable plastic pasteur pipette to charge the chamber with the sample. The cells were pelleted by centrifugation and the density of osteoclasts adjusted to $1.5 \times 10^4$/mL in EMEM medium, supplemented with 10% o fetal calf serum and 1.7 g/liter of sodium bicarbonate. 3 mL aliquots of the cell suspension (per treatment) were decanted into 15 mL centrifuge tubes. These cells were pelleted by centrifugation. To each tube 3 mL of the appropriate treatment was added (diluted to 50 uM in the EMEM medium). Also included were appropriate vehicle controls, a positive control (87MEM1 diluted to 100 ug/mL) and an isotype control (IgG2a diluted to 100 ug/mL). The tubes were incubate at 37° C. for 30 min.

Aliquots (0.5 mL) of the cells were seeded onto sterile dentine slices in a 48-well plate and incubated at 37° C. for 2 h. Each treatment was screened in quadruplicate. The slices were washed in six changes of warm PBS (10 mL/well in a Swell plate) and then placed into fresh treatment or control and incubated at 37° C. for 48 h. The slices were then washed in phosphate buffered saline and fixed in 2% glutaraldehyde (in 0.2M sodium cacodylate) for 5 min., following which they were washed in water and incubated in buffer for 5 min at 37° C. The slices were then washed in cold water and incubated in cold acetate buffer/fast red garnet for 5 min at 4° C. Excess buffer was aspirated, and the slices were air dried following a wash in water.

The TRAP positive osteoclasts were enumerated by bright-field microscopy and were then removed from the surface of the dentine by sonication. Pit volumes were determined using the Nikon/Lasertec ILM21W confocal microscope.

General

Nuclear magnetic resonance spectra were recorded at either 250 or 400 MHz using, respectively, a Bruker AM 250 or Bruker AC 400 spectrometer. $CDCl_3$ is deuteriochloroform, DMSO-$d_6$ is hexadeuteriodimethylsulfoxide, and $CD_3OD$ is tetradeuteriomethanol. Chemical shifts are reported in parts per million (d) downfield from the internal standard tetramethylsilane. Abbreviations for NMR data are as follows: s=singlet, d=doublet, t=triplet, q=quartet, m=multiplet, dd=doublet of doublets, dt=doublet of triplets, app=apparent, br=broad. J indicates the NMR coupling constant measured in Hertz. Continuous wave infrared (IR) spectra were recorded on a Perkin-Elmer 683 infrared spectrometer, and Fourier transform infrared (FIR) spectra were recorded on a Nicolet Impact 400 D infrared spectrometer. IR and FTIR spectra were recorded in transmission mode, and band positions are reported in inverse wavenumbers ($cm^{-1}$). Mass spectra were taken on either VG 70 FE, PE Syx API Im, or VG ZAB HF instruments, using fast atom bombardment (CAB) or electrospray (ES) ionization techniques. Elemental analyses were obtained using a Perkin-Elmer 240 C elemental analyzer. Melting points were taken on a Thomas-Hoover melting point apparatus and are uncorrected. All temperatures are reported in degrees Celsius.

Analtech Silica Gel GF and E. Merck Silica Gel 60 F-254 thin layer plates were used for thin layer chromatography. Both flash and gravity chromatography were carried out on E. Merck Kieselgel 60 (230–400 mesh) silica gel.

Where indicated, certain of the materials were purchased from the Aldrich Chemical Co., Milwaukee, Wis., Chemical Dynamics Corp., South Plainfield, N.J., and Advanced Chemtech, Louisville, Ky.

Methods of Preparation and Specific Examples

Unless otherwise indicated, all of the starting materials were obtained from commercial sources. Without further elaboration, it is believed that one skilled in the art can, using the preceding description, utilize the present invention to its fullest extent. These Examples are given to illustrate the invention, not to limit its scope. Reference is made to the claims for what is reserved to the inventors hereunder.

The following Scheme I illustrates one process for preparing the compounds of this invention.

Scheme 1

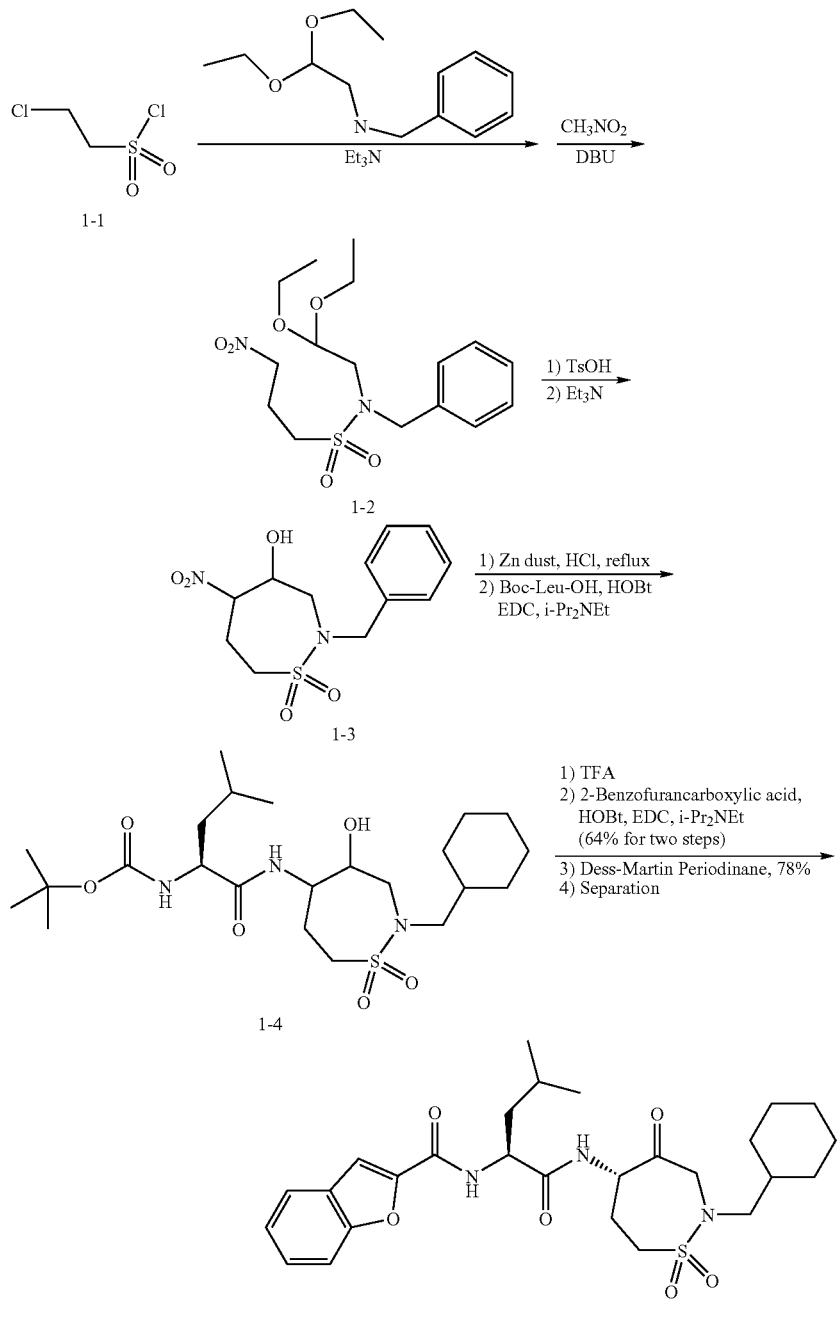

The starting sulfonyl chloride 1-A is available commercially. The sulfonamide 1-2 is prepared by sulfonylation of the acetal (Aldrich) with the sulfonyl chloride 1-1 in the presence of a base such as triethylamine. The sulfonic acid amide is alkylated using nitromethane and DBU. The acetal is deprotected (e.g., p-toluene sulfonic acid) and the crude aldehyde (1-3) is treated with an organic base to effect the nitro-aldol ring closure to provide the 5-nitrothiazepane-4-ol (1-4). The nitro group is reduced with Zn in the presence of HCl followed by coupling of the resulting amine with N-Boc-4-leucine in the presence of a coupling agent common to the art such as EDC. Removal of the N-Boc protecting group under acidic conditions followed by coupling of the resulting amine salt with benzofuran-2-carboxylic acid and oxidation of the alcohol with an oxidizing agent common to the art such as pyridine sulfur trioxide or Dess-Martin periodinane provides a compound of formula 1.

This set of steps can be used to make other compounds of formula 1, by simply varying the starting material or the penultimate ester-forming step. In addition the synthetic processes described in the PCT application having publication number WO 01-70232 published 27 Sep. 2001 can be used to make compounds of this invention as well. Those chemistries are incorporated herein by reference in full.

The following specific examples are provided to illustrate the invention further. They are representative examples, and are not intended to limit the invention. Reference is made to the clams for what is reserved to the inventors hereunder.

EXAMPLES

Example 1

Preparation of Benzofuran-2-carboxylic acid [(S)-1-((S)-2-benzyl-1,1,4-trioxo-1l$^6$-[1,2]thiazepan-5-yl-carbamoyl)-3-methyl-butyl]-amide

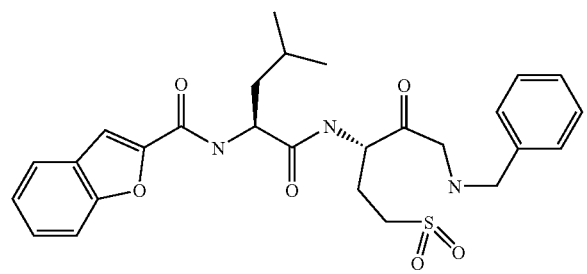

1a. Ethenesulfonic acid benzyl-(2,2-diethoxy-ethyl)-amide

To a solution of benzylamino-acetaldehyde diethyl acetal (14.6 ml, 61.3 mmol) and triethylamine (19.0 ml, 122.0 mmol) in dichloromethane (200 ml) at 0° C. under argon was added 2-chloro-1-ethanesulfonyl chloride (10.0 g, 61.3 mmol). After stirring at rt for 3 h, the reaction mixture was quenched with water (300 ml), extracted with dichloromethane (200 ml×2), washed with brine (150 ml), dried over MgSO$_4$, filtered, and concentrated in vacuo to give the title compound which was used in next step without further purification; $^1$H NMR (CDCl$_3$): 1.23 (t, 6H), 3.22(d, 2H), 353 (m, 2H), 3.72 (m, 2H), 4.52 (s, 12H), 4.63 (t, 1H), 5.88 (d, 1H), 6.23 (d, 1H), 6.50–6.43 (m, 1H), 7.35 (m, 5H); LCMS: 268 (MH$^+$–46).

1b. 3-Nitro-propane-1-sulfonic acid benzyl-(2,2-diethoxy-ethyl)-amide

To a solution of crude ethanesulfonic acid benzyl-(2,2-diethoxy-ethyl)-amide (10 g, 32 mmol) in ethanol (150 ml) under argon was added nitromethane (100 ml) followed by Na-tert-pentoxide (1.8 g, 16 mmol) at rt. After stirring for overnight at ambient temperature, the mixture was concentrated in vacuo, diluted with chloroform (300 ml), washed with cold 1N HCl (200 ml), dried over MgSO$_4$, filtered, and purified on silica gel column (dichloromethane) to give the title compound (5 g, 42% for 2 steps); $^1$H NMR (CDCl$_3$): 1.25 (t, 6H), 2.55 (m, 2H), 3.20 (m, 2H), 3.55 (m, 2H), 3.75 (m, 21), 4.60 (m, 5H), 7.40 (m, 5H); LCMS: 393 (MH$^+$).

1c. 3-Nitro-propane-1-sulfonic acid benzyl-(2-oxo-ethyl)-amide

To a solution of 3-nitro-propane-1-sulfonic acid benzyl-2,2-diethoxy-ethyl)-amide (5.0 g, 13.4 mmol) in acetone (200 ml, 5% v/v water) was added p-toluenesulfonic acid (1.02 g, 5.35 mmol). The reaction mixture was refluxed for overnight, cooled to rt, concentrated in vacuo, diluted with ethyl acetate (250 ml), washed with sat'd NaHCO$_3$ (150 ml), dried over MgSO$_4$, filtered, and concentrated in vacuo to give the crude title compound (4.2 g, 105%) used in next step without further purification; $^1$H NMR (CDCl$_3$): 2.55 (m, 2H), 3.20 (t, 2H), 4.00(s, 2H), 4.42 (s, 2H), 4.55 (t, 2H), 7.35–7.20 (m, 51), 9.40 (s, 1H); LCMS: 301 (MH$^+$).

1d. 2-Benzyl-5-nitro-1,1-dioxo-1l$^6$-[1,2]thiazepan-4-ol

To a solution of crude 3-nitro-propane-1-sulfonic acid benzyl-(2-oxo-ethyl)-amide (4.2 g) in THF (100 ml) was added triethylamine (0.37 ml, 2.67 mmol) at rt. After stirring for 18 hr at rt, the reaction mixture was concentrated in vacuo, and purified by recrystallization in dichloromethane to give the title compound (2.51 g, 63%); $^1$H NMR (CD$_3$OD): 2.80–2.35 (1,2H), 3.65–3.20 (m, 4H), 4.80–4.30 (m, 4H), 7.30 (m, 5H); LCMS: 301 (MH$^+$).

1e. 5-Amino-2-benzyl-1,1-dioxo-1l$^6$-[1,2]thiazepan-4-ol

To a solution of 2-benzyl-5-nitro-1,1-dioxo-1l$^6$-[1,2]thiazepan-4-ol (1.5 g, 5.0 mmol) in MeOH (150 ml) was added concentrated HCl (15 ml) and zinc dust (1.32 g, 12.5 mmol) at rt. After refluxing for 1.5 hr, the reaction mixture was concentrated in vacuo, diluted with water (100 ml), basified to pH (7–10), extracted six times with a solution of 20% ethanol in chloroform (100 ml), dried over MgSO$_4$, filtered, and concentrated in vacuo to yield the crude title compound (1.0 g) used in next step without further purification; LCMS: 271(MH$^+$).

1f. [(S)1-(2-Benzyl-4-hydroxy-1,1-dioxo-1l$^6$-[1,2]thiazepan-5-ylcarbamoyl)-3-methylbutyl]-carbamic acid tert-butyl ester To a solution of 5-amino-2-benzyl-1,1-dioxo-1l$^6$-[1,2]thiazepan 4-ol (0.60 g, 2.22 mmol) in DMF (8 ml) under argon was added BOC-(L)-leucine (0553 g, 2.22 mmol), 1-hydroxybenzotriazole (0.33 g, 2.44 mmol), and EDC-HCl (0.469 g, 2.44 mmol) at RT. After stirring for 18 hr at rt, the reaction mixture was quenched with cold 1N HCl (60 ml), and extracted with ethyl acetate (50 ml×3). The combined organic layer was washed with sat'd NaHCO$_3$, brine, dried over MgSO$_4$, concentrated in-vacuo, and purified on silica gel column (20% to 30% ethyl acetate/hexane) to give the title compound (0.386 g, 27% two steps); $^1$H NMR (CDCl$_3$): 0.98 (m, 6H), 1.46 (s, 9H), 2.15 (m, 2H), 3.20 (m, 1H), 3.50–3.25(m, 2H), 3.70 (m, 1H), 3.85 (m, 1H), 4.0 (m, 1H), 4.15 (m, 1H), 4.54 (d, J=14.8 Hz, 1H), 4.80 (m, J=14.8 Hz, 2H), 7.40–7.30 (m, 5H); LCMS: 484 (MH$^+$).

1g. Benzofuran-2-boxylic acid [(S)-1-((S)-2-benzyl-hydroxy-1,1-dioxo-1l$^6$-[1,2]thiazepan-5-ylcarbamoyl)-3-methyl-butyl]-amide 4M HCl in dioxane (4.0 ml, 15.9 mmol) was added to a solution of [(S)-1-(2-benzylhydroxy-1,1-dioxo-1l$^6$-[1,2]thiazepan-5-ylcarbamoyl)$_3$-methyl-butyl]-carbamic acid tert-butyl ester (0.382 g, 0.79 mmol) in MeOH (5 ml) and stirred for 1.5 hr at RT. The mixture was then concentrated in vacuo and azeotroped with toluene three times (10 ml×3). Then half the solid (182 mg, 0.40 mmol) was dissolved in DMF (3 ml) followed by the addition of 2-benzofurancarboxylic acid (70.5 mg, 0.44 mmol), 1-hydroxybenzotriazole (64 mg, 0.48 mmol), EDC-HCl (91 mg, 0.48 mmol), and N,N-isopropylethylamine (0.180 ml, 1.02 mmol). After stirring for 18 hr at rt, the reaction mixture was quenched with cold 1N HCl (40 ml), and extracted with ethyl acetate (50 ml×3). The combined organic layer was washed with sat'd NaHCO$_3$, brine, dried over MgSO$_4$, and concentrated in vacuo. The residue was purified on silica gel column (25% to 30% ethyl acetate/hexane) to give the title compound (135 mg, 64% for 2 steps). $^1$H NMR (CDCl$_3$): 1.0 (m, 6H), 1.90–1.70 (m, 3H), 2.15 (m, 2H), 3.50–3.10 (m, 3H), 3.90–3.65 (m, 1H), 3.90 (m, 1H), 4.25–4.05 (m, 1H), 4.60–4.45 (m, 2H), 4.77 (d, J=14.7 Hz, 1H), 7.10–6.90 (m, 2H), 755–7.28 (m, 9H), 7.69 (d, J=7.7 Hz, 1H); LCMS: 528(MH$^+$).

1h. Benzofuran-2-carboxylic acid [(S)-1-((S)-2-benzyl-1,1,4-trioxo-1l$^6$-[1,2]thiazepan-5-ylcarbamoyl)-3-methyl-butyl]-amide Dess-Martin periodinane (150 mg, 0.353 mmol) was added to a solution of benzofuran-2-carboxylic acid [(S)-1-((S)-2-benzyl-1-hydroxy-1,1-dioxo-1l$^6$-[1,2]thiazepan-5-ylcarbamoyl)-3-methyl-butyl]-amide (124 mg, 0.235 mmol) in dichloromethane (8 ml) and stirred at RT for 1.5 hr. The reaction was then quenched with 10% aq. Na$_2$S$_2$O$_3$ (10 ml) and sat'd NaHCO$_3$ (10 ml). The aqueous layer was extracted with CH$_2$Cl$_2$ (10 ml) and the combined organic layers were washed with brine, dried over MgSO$_4$, and concentrated in vacuo. The residue was purified by silica gel column (20% to 25% ethyl acetate/hexane) to give the title compound (96 mg, 78%) as a mixture of diastereomers. The diastereomers were separated using a chiral HPLC column (R,R-Whelko on Gilson HPLC) to give 30.6 mg of the first eluting compound as a desired diastereomer and 31.3 mg of the second eluting compound as an undesired diastereomer; $^1$H NMR (CDCl$_3$): 0.90 (m, 6H), 1.70 (m, 3H), 3.35 (m, 2H), 350 (d, 1H), 4.20–4.10 (m, 2H), 450 (m, 1H), 4.60 (m, 1H), 4.80(d, 1H), 6.85 (m, 1H), 7.10 (m, 1H), 7.50–7.15 (m, 9H), 7.65 (d, 1H); LCMS: 526 (MH$^+$).

Example 2

Preparation of Benzofuran-2-carboxylic acid [(S)-1-(S)-2-cyclohexylmethyl-1,1,4-trioxo-1l$^6$-[1,2]thiazepan-5-ylcarbamoyl)-3-methyl-butyl]-amide

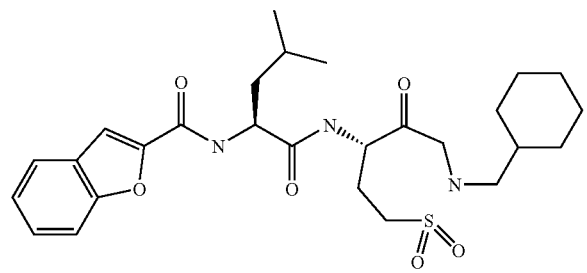

Following the procedure of Example 1 (a), except substituting benzylmethyl-aminoacetaldehyde dimethyl acetal for cyclohexylmethyl-aminoacetaldehyde dimethyl acetal, the title compound was obtained; $^1$H NMR (CDCl$_3$, 400 MHz) □: 0.70–1.80 (m, 20H), 1.90–2.10 (m, 1H), 2.15 (m, 1H), 2.80 (m, 1H), 3.20–3.35 (m, 3H), 3.60 (d, J=19.2 Hz, 1H), 4.29 (d, J=19.2 Hz, 1H), 4.50–4.65 (m, 2H), 6.85 (d, J=7.96 Hz, 1H), 7.10 (d, J=6.28 Hz, 1H), 7.20–7.45 (m, 4H), 7.61 (d, J=8.56 Hz, 1H); LCMS: 532 (MH$^+$).

What is claimed is:

1. A compound according to Formula I,

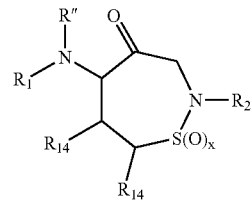

wherein:
x is 0, 1 or 2;
R$_1$ is either formula A or B

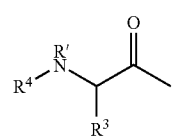
(A)

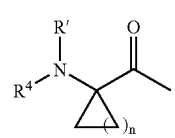
(B)

wherein, in formula (B), n is an integer from 1 to 5;
R$_2$ is H, C$_{1-6}$alkyl, C$_{3-6}$cycloalkyl-C$_{0-6}$alkyl, Ar—C$_{0-6}$alkyl, Het-C$_{0-6}$alkyl R$_9$C(O)—, R$_9$C(S)—, R$_9$SO$_2$—, R$_9$OC(O)—,

R$_9$R$_{11}$NC(O)—, R$_9$R$_{11}$NC(S)—, R$_9$(R$_{11}$)NSO$_2$—,

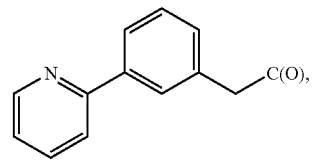

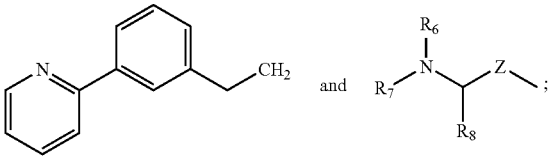

R$_3$ is H, C$_{1-6}$alkyl, C$_{3-6}$cycloalkyl-C$_{0-6}$alkyl, C$_{2-6}$alkenyl, C$_{2-6}$alkynyl, HetC$_{0-6}$alkyl, ArC$_{0-6}$alkyl, Ar—ArC$_{0-6}$alkyl, Ar-HetC$_{0-6}$alkyl, Het-ArC$_{0-6}$alkyl, or Het-HetC$_{0-6}$ alkyl;

R$_4$ is H, C$_{1-6}$alkyl, C$_{3-6}$cycloalkyl-C$_{0-6}$alkyl, Ar—C$_{0-6}$alkyl, Het-C$_{0-6}$alkyl, R$_{14}$C(O)—, R$_{14}$—C(S)—, R$_{14}$SO$_2$—, R$_{14}$OC(O)—, R$_{14}$R$_{13}$NC(O)—, R$_{14}$R$_{13}$NC(S)—, or R$_{14}$R$_{13}$NSO$_2$;

R$_5$ is H, C$_{1-6}$alkyl, OC$_{1-4}$alkyl, SC$_{1-4}$alkyl, N(R$_9$)$_2$, CH$_2$OC$_{1-4}$, CH$_2$SC$_{1-4}$, or CH$_2$N(R$_9$)$_2$;

$R_6$ is H, $C_{1-6}$alkyl, $C_{3-6}$cycloalkyl-$C_{0-6}$alkyl, Ar—$C_{0-6}$alkyl, or Het-$C_{0-6}$alkyl;

$R_7$ is H, $C_{1-6}$alkyl, $C_{3-6}$cycloalkyl-$C_{0-6}$alkyl, Ar—$C_{0-6}$alkyl, Het-$C_{0-6}$alkyl, $R_{10}$C(O)—, $R_{10}$C(S)—, $R_{10}$SO$_2$—, $R_9$OC(O)—, $R_{10}R_{13}$NC(O)—, or $R_{10}R_{13}$NC(S)—;

$R_8$ is H, $C_{1-6}$alkyl, $C_{2-6}$alkenyl, $C_{2-6}$alkynyl, Ar—$C_{0-6}$alkyl or Het-$C_{0-6}$alkyl;

$R_9$ is H, $C_{1-6}$alkyl, $C_{2-6}$alkenyl, $C_{2-6}$alkynyl, Ar—$C_{0-6}$alkyl or Het-$C_{0-6}$alkyl;

$R_{10}$ is $C_{1-6}$alkyl, $C_{3-6}$cycloalkyl-$C_{0-6}$alkyl, Ar—$C_{0-6}$alkyl or Het-$C_{0-6}$alkyl;

$R_{11}$ is H, $C_{1-6}$alkyl, Ar—$C_{0-6}$alkyl, $C_{3-6}$cycloalkyl-$C_{0-6}$alkyl, or Het-$C_{0-6}$alkyl;

$R_{12}$ is H, $C_{1-6}$alkyl, Ar—$C_{0-6}$alkyl, or Het-$C_{0-6}$alkyl;

$R_{13}$ is H, $C_{1-6}$alkyl, Ar—$C_{0-6}$alkyl, or Het-$C_{0-6}$alkyl;

$R_{14}$ is H, $C_{1-6}$alkyl, $C_{2-6}$alkenyl, $C_{2-6}$alkynyl, $C_{3-6}$cycloalkyl-$C_{0-6}$alkyl, $C_{1-6}$alkanoyl, Ar—$C_{0-6}$alkyl or Het-$C_{0-6}$alkyl;

R' is H, $C_{1-6}$alkyl, Ar—$C_{0-6}$alkyl, or Het-$C_{0-6}$alkyl;

R" is H, $C_{1-6}$alkyl, Ar—$C_{0-6}$alkyl, or Het-$C_{0-6}$alkyl; or

Z is C(O) or CH$_2$; or a pharmaceutically acceptable salt, hydrate or solvate thereof.

2. A compound according to claim 1 wherein $R_1$ is

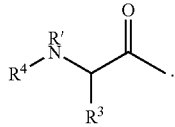

I(A)

3. A compound according to claim 1 wherein X is 0 or 2.

4. A compound according to claim 2 wherein $R_3$ is $C_{1-6}$alkyl, $C_{3-6}$cycloalkyl-$C_{0-6}$alkyl, or Ar$C_{0-6}$alkyl.

5. A compound according to claim 2 wherein $R_3$ is H, methyl, ethyl, n-propyl, prop-2-yl, n-butyl, isobutyl, but-2-yl, cyclopropylmethyl, cyclohexylmethyl 2-methanesulfinyl-ethyl, 1-hydroxyethyl, toluyl, naphthalen-2-ylmethyl, benzyloxymethyl, and hydroxymethyl.

6. A compound according to claim 2 wherein $R_3$ is toluyl, isobutyl or cyclohexylmethyl.

7. A compound according to claim 2 wherein $R_3$ is isobutyl.

8. A compound according to claim 1 wherein $R_4$ is $R_5$C(O)—, $R_5$C(S)—, $R_{14}$—SO$_2$—.

9. A compound according to claim 8 wherein $R_5$ is $C_{1-6}$alkyl, $C_{2-6}$alkenyl, $C_{3-6}$cycloalkyl-$C_{0-6}$alkyl, $C_{2-6}$-alkanonyl Ar—$C_{0-6}$alkyl, or Het-$C_{0-6}$alkyl.

10. A compound according to claim 9 wherein $R_5$ is:
methyl, halogenated methyl, $C_{1-6}$ alkoxy and aryloxy substituted methyl, heterocycle substituted methyl;
butyl, aryl substituted butyl;
isopentyl;
cyclohexyl;
butenyl, aryl substituted butenyl;
pentanonyl;
phenyl, phenyl substituted with one or more halogens, phenyl substituted with one or more $C_{1-6}$alkoxy groups, phenyl substituted with one or more sulfonyl groups;
benzyl;
naphthylenyl;
benzo[1,3]dioxolyl;

furanyl, halogen substituted furanyl, aryl substituted furanyl;
tetrahydrofuranyl;
benzofuranyl, $C_{1-6}$alkoxy substituted benzofuranyl, halogen substituted benzofuranyl, $C_{1-6}$alkyl substituted benzofuranyl;
benzo[b]thiophenyl, $C_{1-6}$alkoxy substituted benzo[b]thiophenyl;
quinolinyl;
quinoxalinyl; 1,8-naphthyridinyl;
indolyl, $C_{1-6}$alkyl substituted indolyl;
pyridinyl, $C_{1-6}$alkyl substituted pyridinyl, 1-oxy-pyridinyl;
furo[3,2-b]pyridinyl, $C_{1-6}$alkyl substituted furo[3,2-b]pyridinyl;
thiophenyl, $C_{1-6}$alkyl substituted thiophenyl, halogen substituted thiophenyl;
thieno[3,2-b]thiophenyl;
isoxazolyl, $C_{1-6}$alkyl substituted isoxazolyl; or
oxazolyl.

11. A compound according to claim 10 wherein $R_5$ is:
4-pentanonyl;
naphthylen-2-yl;
benzo[1,3]dioxol-5-yl,
tetrahydrofuran-2-yl
furan-2-yl;
benzofuran-2-yl;
benzo[b]thiophen-2-yl;
quinolin-2-yl, quinolin-3-yl, quinolin-4-yl, quinolin-6-yl, and quinolin-8-yl;
quinoxalin-2-yl;
1,8-naphthyridin-2-yl;
indol-3-yl, indol-5-yl;
pyridin-2-yl, pyridin-5-yl;
furo[3,2-b]pyridin-2-yl;
thiophen-3-yl;
thieno[3,2-b]thiophene-2-yl;
isoxazol-4-yl; or
oxazol-4-yl.

12. A compound according to claim 1 wherein formula I is

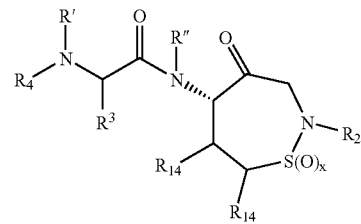

wherein each $R_{14}$ is hydrogen.

13. A compound according to claim 12 which is:
benzofuran-2-carboxylic acid [(S)-1-(S)-2-benzyl-1,1,4-trioxo-1l$^6$-[1,2]thiazepan-5-ylcarbamoyl)3-methyl-butyl]-amide;
benzofuran-2-carboxylic acid [(S)-1-((S)-2-cyclohexylmethyl-1,1,4-trioxo-1l$^6$-[1,2]thiazepan-5-ylcarbamoyl)-3-methyl-butyl]-amide; or
a pharmaceutically acceptable salt thereof.

14. A pharmaceutical preparation comprising a compound according to claim 1 and a pharmaceutically acceptable excipient.

* * * * *